United States Patent
Olsen

(10) Patent No.: US 6,743,831 B2
(45) Date of Patent: Jun. 1, 2004

(54) IMPLANTABLE MEDICAL CATHETER HAVING REINFORCED SILICONE ELASTOMER COMPOSITION

(75) Inventor: James M. Olsen, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 73 days.

(21) Appl. No.: 10/128,000

(22) Filed: Apr. 23, 2002

(65) Prior Publication Data

US 2003/0199630 A1 Oct. 23, 2003

(51) Int. Cl.⁷ ................................................. C08L 83/00
(52) U.S. Cl. ........................... 523/105; 528/15; 528/31; 528/32; 524/433; 524/588
(58) Field of Search ............................. 528/15, 31, 32; 524/423, 436, 588, 433; 422/9.41, 422; 523/105

(56) References Cited

U.S. PATENT DOCUMENTS

| | | |
|---|---|---|
| 4,055,682 A | 10/1977 | Merrill |
| 5,908,878 A * | 6/1999 | Baity et al. ................. 523/203 |
| 5,948,539 A | 9/1999 | Paulsen et al. |
| 6,040,369 A | 3/2000 | Paulsen et al. |
| 6,080,829 A | 6/2000 | Tapsak et al. |

OTHER PUBLICATIONS

Helen Kazemi–Shirazi et al., "New Silicone Rubber 2, Biocompatible Silicone Rubbers"; Die Angewandt Makromolekulare Chemi 203 (1993) p. 193–201. Institute of Chemical Technology of Organic Materials, Vienna University of Technology, Getreidemark, 9/162, A–1060 Vienna, Austria.

International Search Report dated Sep. 4, 2003.

* cited by examiner

Primary Examiner—Margaret G. Moore
Assistant Examiner—Marc S. Zimmer
(74) Attorney, Agent, or Firm—Banner & Witcoff, Ltd.

(57) ABSTRACT

An implantable medical catheter comprising at least one fluid passageway and a cured elastomer composition is disclosed. The cured elastomer composition is obtained by cross-linking an uncured blend composition that comprises an intimately admixed mixture that comprises the following components: (A) silica that had been silyliated by treatment and contains trialkylsilyl groups; (B) a polysiloxane copolymer; (C) a catalyst, and (D) an organohydrogen polysiloxane cross-linker, the catalyst and the cross-linker being present in the uncured blend composition in sufficient amount to cause the cross-linking reaction to occur.

21 Claims, 4 Drawing Sheets

IMPLANTABLE MEDICAL CATHETER HAVING REINFORCED SILICONE ELASTOMER COMPOSITION

RELATED APPLICATION

Not applicable.

FIELD OF THE INVENTION

The present invention is directed to medical catheters having improved mechanical properties.

BACKGROUND OF THE INVENTION

Various types of materials are used for catheters, such as Dow Corning HP (high performance) or Dow Corning ETR (extra tear resistance) material. These types of materials have relatively high tear resistance. However, it would be desirable to have a catheter material that had a higher crush and creep resistance than Dow Corning HP or Dow Corning ETR.

Crush resistance and creep resistance are important properties for catheters because they can be subjected to various forces, such as compression and stretching forces after they are implanted within a patient. For example, a catheter that is implanted within a patient so that it can come into contact with the spinous processes can be frequently subjected to compression from the spinous processes.

Other materials have higher crush and creep resistance than Dow Corning HP and Dow Corning ETR. An example of such a material is Dow Corning MDX. While this type of material has relatively high crush and creep resistance, it is not considered to be suitable material for a catheter because a higher tear resistance material is believed to be necessary for such a catheter.

Tear resistance is important for catheters because they can be "nicked" or cut on the introducer needle during placement. Notably, this can occur without the physician implanting the catheter knowing that a nick or cut had occurred. Tear resistance is a mechanical property that indicates how quickly a cut or tear progresses to a fracture or break.

As it will be readily appreciated by those skilled in the art of medical catheters, certain mechanical properties, such as tear strength, abrasion resistance, resistance to shredding, compression set, crush and creep resistance are of great importance in the materials for any catheter device that is implanted into the human body. It should also be readily appreciated by those skilled in the art that catheters having improved mechanical properties, and particularly improved tear resistance, crush resistance and creep resistance provide higher performance and better results than catheters having lesser such mechanical properties.

The need still exists for catheters having improved mechanical properties, including improved tear resistance, crush resistance and creep resistance. The present invention provides such a catheter.

SUMMARY OF THE INVENTION

It is an object of the present invention to provide a catheter having improved overall mechanical properties over prior catheters.

It is another object of the present invention to provide tubular material for implantable medical catheters, which material has improved overall mechanical properties, including improved tear resistance, crush resistance and creep resistance.

The implantable medical catheter disclosed herein attains the foregoing and other objects of the present invention. More specifically, the implantable medical catheter of the present invention comprises a catheter defining at least one fluid passageway and a cured elastomer composition obtained by cross-linking an uncured blend composition that comprises an intimately admixed mixture that comprises the following components: (A) silica that had been silyliated by treatment and contains trialkylsilyl groups comprising approximately 23 to 45 percent by weight of the mixture; (B) a polysiloxane copolymer composed of divalent —$R_1R_2SiO$—, divalent —$R_3R_4SiO$— and end-blocking $R_5R_6R_7SiO$— units, comprising approximately 55 to 77 percent by weight of the mixture, where $R_1$ and $R_2$ independently are lower alkyl of 1 to 6 carbons, phenyl or trifluoropropyl, $R_3$ is vinyl, allyl, or other olefinic group having up to 4 carbons, $R_4$ is lower alkyl of 1 to 6 carbons, phenyl or trifluoropropyl, and $R_5$, $R_6$, and $R_7$ independently are lower alkyl of 1 to 6 carbons, phenyl, vinyl, allyl, or other olefinic group having up to 4 carbons and one double bond, the polysiloxane copolymer has a degree of polymerization (D.P.) approximately in the range of 3500 to 6500, and the olefin containing —$R_3R_4SiO$— groups are present randomly distributed in the polysiloxane copolymer and approximately in the 0.05 to 0.3 mol percent range, with the provisos that when $R_1$, or $R_2$, or both represent phenyl groups then proportion of the phenyl-containing divalent siloxane units does not exceed 15 mol percent and when $R_1$ or $R_2$ or both represent trifluoropropyl groups, then the proportion of the trifluoropropyl-containing divalent siloxane units does not exceed approximately 40 mol percent in the polysiloxane copolymer; (C) a catalyst, and (D) an organohydrogen polysiloxane cross-linker, the catalyst and the cross-linker being present in the uncured blend composition in sufficient amount to cause the cross-linking reaction to occur.

In one embodiment, the polysiloxane copolymer, the —$R_1R_2SiO$— group is —$R(CH_3)_2SiO$—, the —$R_3R_4SiO$— group is —$CH_3(CH_2\!=\!CH)SiO$—, and the $R_5R_6R_7SiO$— group is —$(CH_3)_2(CH_2\!=\!CH)SiO$—.

In one embodiment, the —$CH_3(CH_2\!=\!CH)SiO$— group is present in the proportion of 0.142 mol percent in the polysiloxane copolymer.

In one embodiment, the silyliated silica includes trimethylsilyl groups in such quantity that the carbon content of the silyliated silica is in the range of approximately 4 to 8 percent by weight of the silyliated silica.

In one embodiment, the carbon content of the silyliated silica is approximately 7.3 percent by weight of the silyliated silica.

In one embodiment, the catheter includes barium sulfate ($BaSO_4$).

DETAILED DESCRIPTION OF THE PREFERRED EMBODIMENTS

Figure 1:
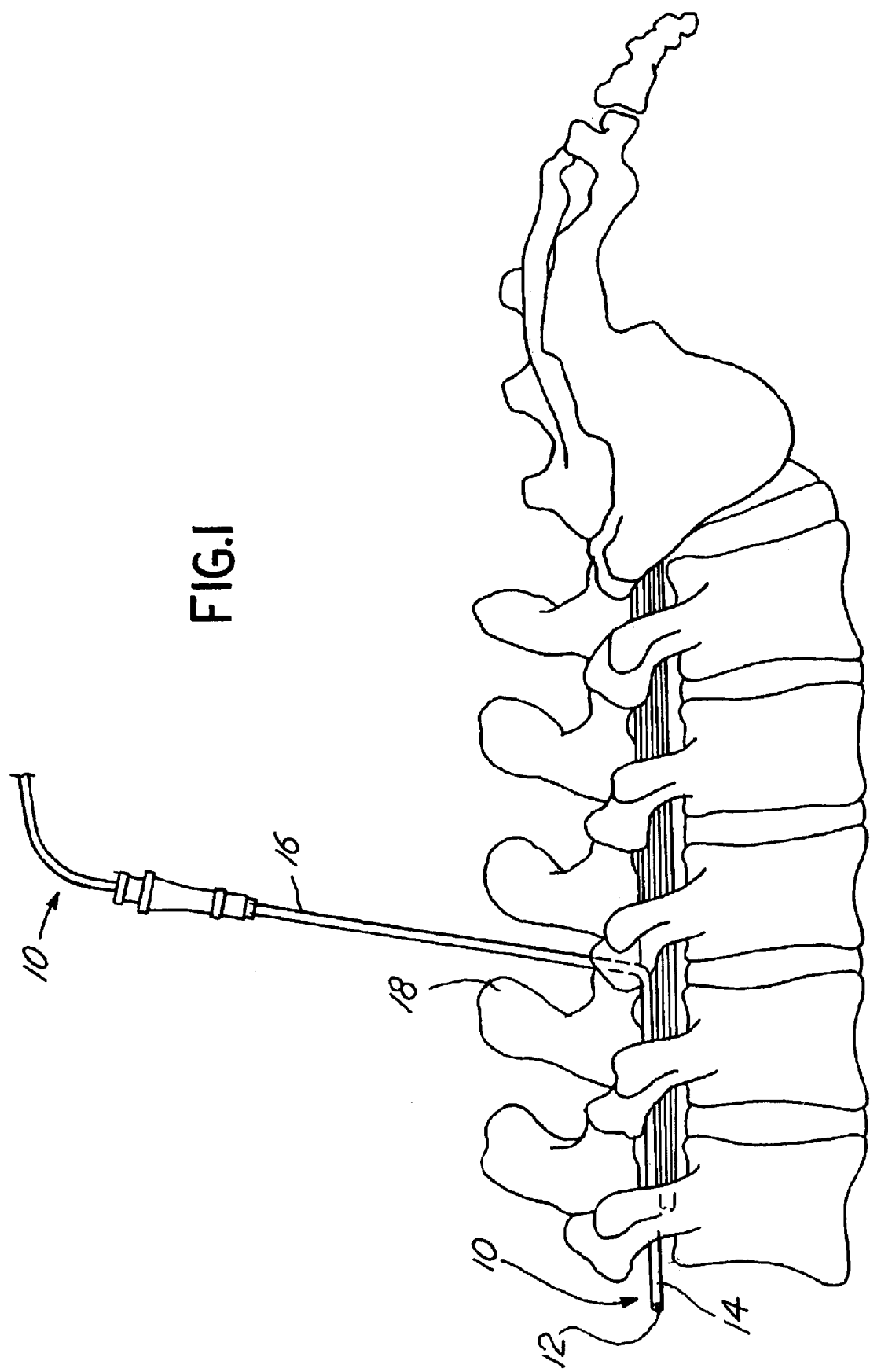
FIG. 1 illustrates an embodiment of the present invention that is implanted within a patient and can come into contact with the spinous processes of the patient.

The implantable medical catheter of the present invention comprises a catheter 10 defining at least one fluid passageway 12 and a cured elastomer composition 14. As shown in FIG. 1, the catheter 10 is implanted within a patient using an introducer needle 16. FIG. 1 shows that catheter 10 is implanted so that it can come into contact with spinous processes 18 of the patient.

The cured elastomer composition 14 is obtained by cross-linking an uncured blend composition that comprises an intimately admixed mixture that comprises the following components: (A) silica that had been silyliated by treatment and contains trialkylsilyl groups comprising approximately 23 to 45 percent by weight of the mixture; (B) a polysiloxane copolymer composed of divalent —$R_1R_2SiO$—, divalent —$R_3R_4SiO$— and end-blocking $R_5R_6R_7SiO$— units, comprising approximately 55 to 77 percent by weight of the mixture, where $R_1$ and $R_2$ independently are lower alkyl of 1 to 6 carbons, phenyl or trifluoropropyl, $R_3$ is vinyl, allyl, or other olefinic group having up to 4 carbons, $R_4$ is lower alkyl of 1 to 6 carbons, phenyl or trifluoropropyl, and $R_5$, $R_6$, and $R_7$ independently are lower alkyl of 1 to 6 carbons, phenyl, vinyl, allyl, or other olefinic group having up to 4 carbons and one double bond, the polysiloxane copolymer has a degree of polymerization (D.P.) approximately in the range of 3500 to 6500, and the olefin containing —$R_3R_4SiO$— groups are present randomly distributed in the polysiloxane copolymer and approximately in the 0.05 to 0.3 mol percent range, with the provisos that when $R_1$, or $R_2$, or both represent phenyl groups then proportion of the phenyl-containing divalent siloxane units does not exceed 15 mol percent and when $R_1$ or $R_2$ or both represent trifluoropropyl groups, then the proportion of the trifluoropropyl-containing divalent siloxane units does not exceed approximately 40 mol percent in the polysiloxane copolymer; (C) a catalyst, and (D) an organohydrogen polysiloxane cross-linker, the catalyst and the cross-linker being present in the uncured blend composition in sufficient amount to cause the cross-linking reaction to occur.

In one embodiment, the polysiloxane copolymer, the —$R_1R_2SiO$— group is —$(CH_3)_2SiO$—, the —$R_3R_4SiO$— group is $CH_3(CH_2=CH)SiO$—, and the $R_5R_6R_7SiO$— group is —$(CH_3)_2(CH_2=CH)SiO$—.

In one embodiment, the —$CH_3(CH_2=CH)SiO$— group is present in the proportion of 0.142 mol percent in the polysiloxane copolymer.

In one embodiment, the silyliated silica includes trimethylsilyl groups in such quantity that the carbon content of the silyliated silica is in the range of approximately 4 to 8 percent by weight of the silyliated silica.

In one embodiment, the carbon content of the silyliated silica is approximately 7.3 percent by weight of the silyliated silica.

In one embodiment, the catheter includes barium sulfate ($BaSO_4$). The barium sulfate provides a radiopacity feature to the catheter of the present invention. In a preferred embodiment, the catheter of the present invention comprises about 13% by weight barium sulfate.

U.S. Pat. Nos. 5,948,539 and 6,040,369 are incorporated herein by reference. More specifically, FIG. 2 and Col. 2, line 40 through Col. 11, line 3 of U.S. Pat. No. 5,948,539, and FIG. 2 and Col. 2, line 40 through Col. 11, line 3 of U.S. Pat. No. 6,040,369 are incorporated herein by reference. Thus, the elastomeric compositions and the methods of making those elastomeric compositions disclosed in U.S. Pat. Nos. 5,948,539 and 6,040,369 are incorporated herein by reference. These patents disclose a medical electrical lead and reinforced silicone elastomer compositions used therein. These patents disclose the reinforced silicone elastomer compositions for use as insulator for electrical leads of implantable medical devices, and which have improved overall mechanical properties over prior art insulators for leads. However, it was not expected that use of these reinforced elastomer compositions as a catheter material would provide a difference in kind over catheters not having the reinforced elastomer compositions of the present invention.

The following test data shows the unexpected and surprising difference in kind between a catheter having the reinforced elastomer compositions of the present invention over catheters not having the reinforced elastomer compositions of the present invention.

EXAMPLE 1

Figure 2:
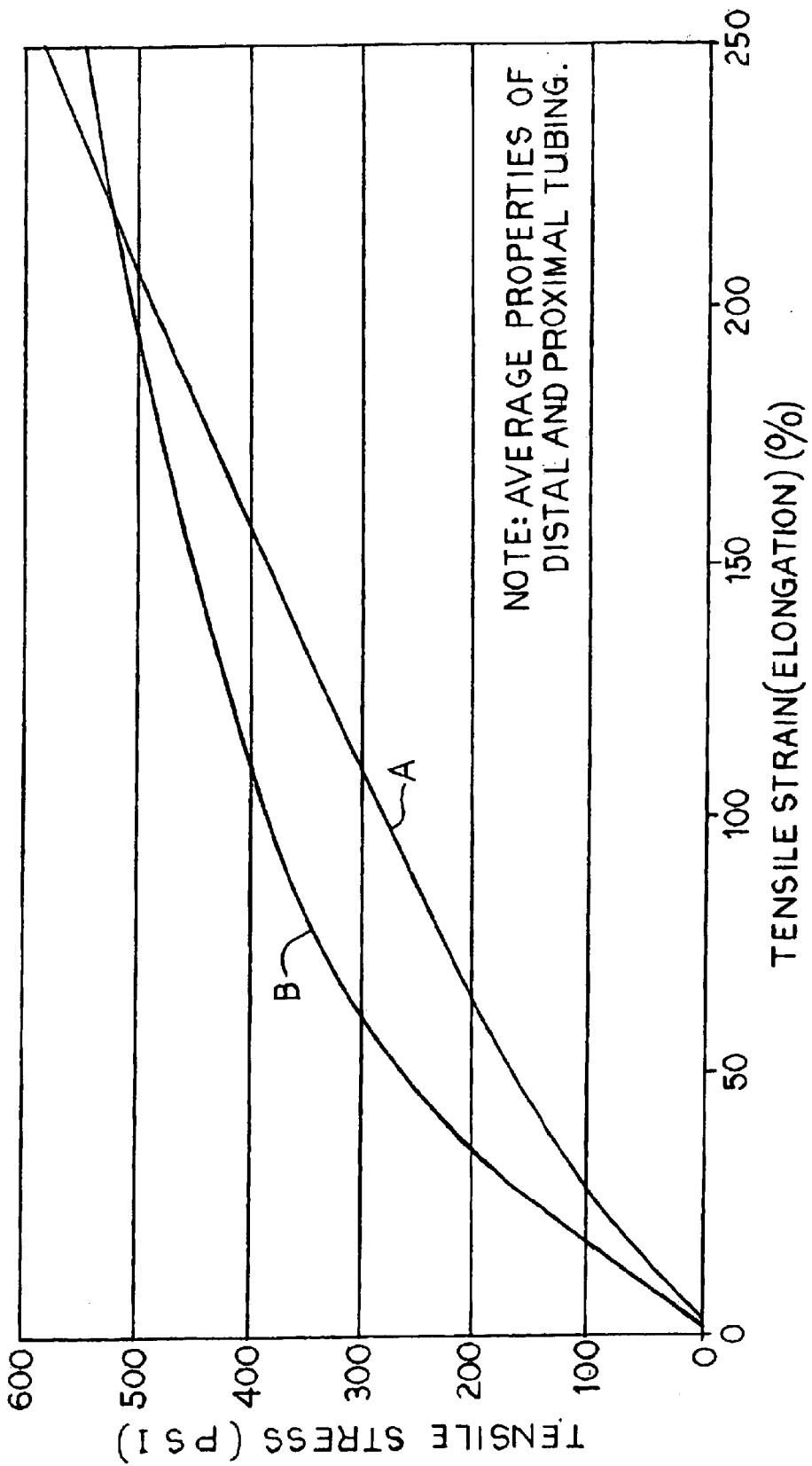
FIG. 2 is a graph illustrating tensile stress (psi) versus tensile strain (%) for a catheter of the present invention versus a prior art catheter.

FIG. 2 is a graph illustrating tensile stress (psi) versus tensile strain (%) for a catheter of the present invention versus a prior art catheter having the same dimensions (i.e., outside and inside diameters, and length). The catheter of the present invention used in this example was made with a material made in the same manner as described in the "Specific Example" in U.S. Pat. Nos. 5,948,539 and 6,040,369, which are incorporated herein by reference. The prior art catheter used in this example was made using Dow Corning ETR, and had the same outside and inside diameters as the catheter of the present invention. Both of these catheters also included 13% by weight barium sulfate by mixing barium sulfate in a suitable amount and manner prior to or during the forming of the catheters. Two different sizes of both catheters were made—a distal tubing (having an inside diameter of 0.021 inches and an outside diameter of 0.055 inches) and a proximal tubing (having an inside diameter of 0.021 inches and an outside diameter of 0.085 inches).

Tensile strain per unit stress, sometimes called axial stiffness, is an elongation property. As shown in FIG. 2, between a tensile strain of 0% to about 200%, the catheter of the present invention (identified as line "A," which is an average of the distal and proximal tubing made in accordance with the present invention) is more elastic than a prior art catheter (identified as line "B," which is an average of the distal and proximal tubing made using Dow Corning ETR). In other words, less force, i.e., tensile stress (psi) is needed to achieve a tensile strain up to about 200% for the catheter of the present invention over a prior art catheter. This is an unexpected and surprising result because the catheter of the present invention, as shown below, also has better crush resistance and creep resistance (i.e., toughness) than the prior art catheter. Typically, the tougher a material is, the less elastic the material is. Thus, it was unexpected and surprising that the catheter of the present invention has superior toughness and elasticity over the prior art catheter between a tensile strain of 0% to about 200%. Moreover, these results were unexpected and surprising in view of the presence of 13% by weight barium sulfate, which would be expected to reduce crush and creep resistance and increase axial stiffness.

Figure 4:
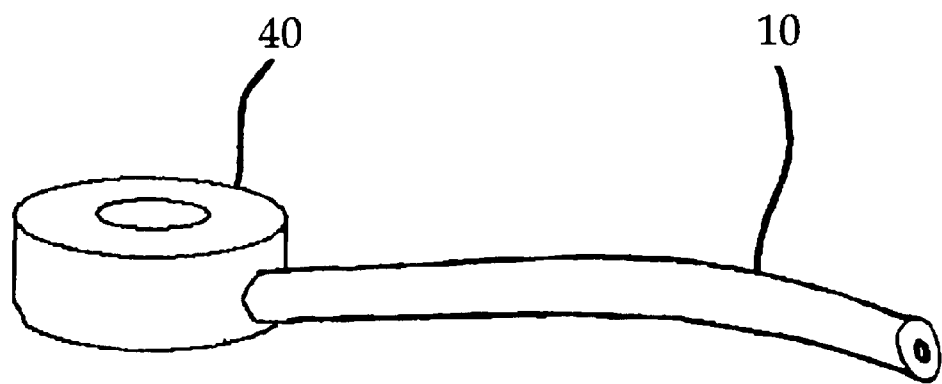
FIG. 4 illustrates an access port connected to a catheter of the present invention.
Figure 5:
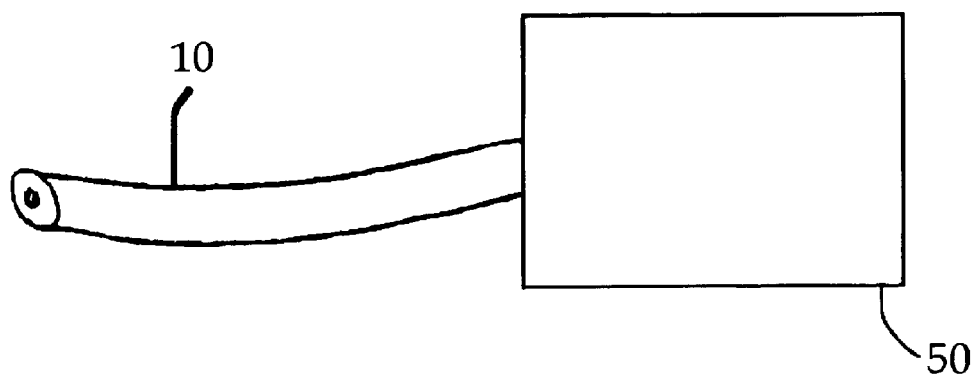
FIG. 5 illustrates a puma connected to a catheter of the present invention.

Since an implanted catheter typically does not experience a tensile strain or elongation of more than 50%, the catheter of the present invention provides a substantial improvement over the prior art catheter in the applicable range of tensile strain or elongation. At a tensile strain of about 50%, the tensile stress for the catheter of the present invention is about 35% lower than the tensile stress of a prior art catheter made with Dow Corning ETR. This means, for example, that for a catheter of the same dimensions (outside and inside diameters), the force at the spinal anchor (not shown) due to the independent motion of an implantable fluid access port 40 (as shown in FIG. 4) or implantable pump 50 (as shown in FIG. 5) will be about 35% less for the catheter of the present invention than for a prior art catheter made with Dow Corning ETR. Since the catheter of the present invention has this improved property over prior art catheters, the catheter of the present invention will be less likely to become dislodged from the spine than prior art catheters.

The crush resistance of the catheter of the present invention and the prior art catheter were also compared. More specifically, the crush resistance of the two catheters having the same dimensions, and both including 13% by weight barium sulfate, were compared by subjecting each catheter to 50% compression during cyclic loading. Crush resistance is defined herein as the number of cycles of compressing each catheter so that the two walls of each catheter were compressed to the thickness of one wall of the catheter until large cracks appeared. This test is designed to simulate the loading for the midline placement of a catheter within a patient's spine where it is compressed between spinous processes, and/or simulate the loading of a vascular catheter between the clavicle and the first rib of a patient. In this test, the catheter of the present invention had a crush resistance of more than 20 times greater than the crush resistance of the prior art catheter.

Figure 3:
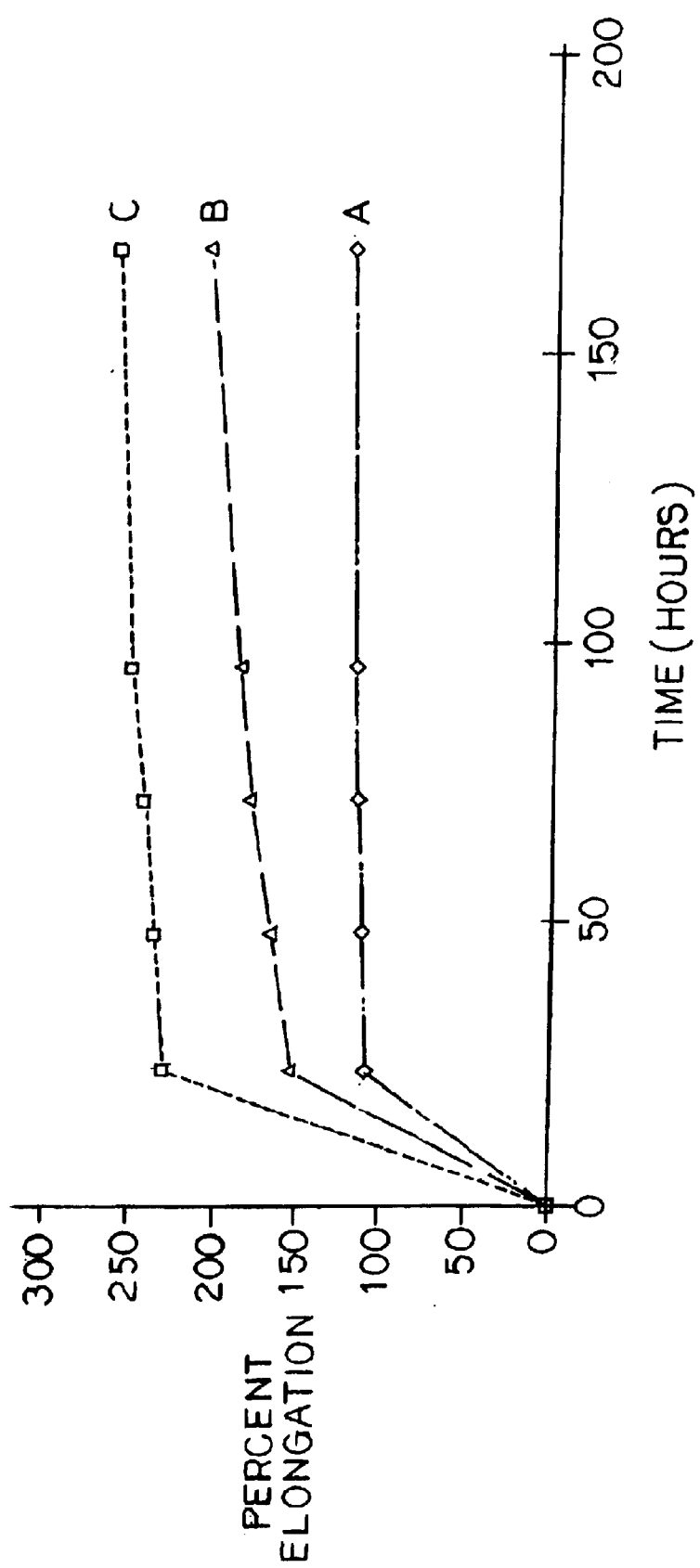
FIG. 3 is a graph illustrating creep resistance for the elastomer of the present invention versus two prior art materials.

The creep resistance for the elastomer of the present invention and two prior art materials Dow Corning ETR and Dow Corning MDX were also compared. The creep resistance of the three materials was compared by subjecting each material to an applied load over time. Creep resistance is defined herein as the resistance to strain or elongation under an applied load over time. As shown in FIG. 3, the elastomer of the present invention (identified as line "A") had substantially more resistance to strain under an applied load than the prior art Dow Corning ETR (identified as line "B") or the prior art Dow Corning MDX (identified as line "C").

The Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which are also intended to be within the scope of the invention. Therefore, the scope of the present invention should be interpreted solely from the following claims, as such claims are read in light of the disclosure.

I claim:

1. An implantable medical catheter, the catheter having at least one fluid passageway and comprising a cured elastomer composition obtained by cross-linking an uncured blend composition that comprises an intimately admixed mixture that comprises the following components:

(A) silica that had been silyliated by treatment and contains trialkylsilyl groups comprising approximately 23 to 45 percent by weight of the mixture;

(B) a polysiloxane copolymer composed of divalent —$R_1R_2SiO$—, divalent —$R_3R_4SiO$— and end-blocking $R_5R_6R_7SiO$— units, comprising approximately 55 to 77 percent by weight of the mixture, where $R_1$ and $R_2$ independently are lower alkyl of 1 to 6 carbons, phenyl or trifluoropropyl, $R_3$ is vinyl, allyl, or other olefinic group having up to 4 carbons, $R_4$ is lower alkyl of 1 to 6 carbons, phenyl or trifluoropropyl, and $R_5$, $R_6$, and $R_7$ independently are lower alkyl of 1 to 6 carbons, phenyl, vinyl, allyl, or other olefinic group having up to 4 carbons and one double bond, the polysiloxane copolymer has a degree of polymerization (D.P.) approximately in the range of 3500 to 6500, and the olefin containing —$R_3R_4SiO$— groups are present randomly distributed in the polysiloxane copolymer and approximately in the 0.05 to 0.3 mol percent range, with the provisos that when $R_1$, or $R_2$, or both represent phenyl groups then proportion of the phenyl-containing divalent siloxane units does not exceed 15 mol percent and when $R_1$ or $R_2$ or both represent trifluoropropyl groups, then the proportion of the trifluoropropyl-containing divalent siloxane units does not exceed approximately 40 mol percent in the polysiloxane copolymer;

(C) a catalyst;

(D) an organohydrogen polysiloxane cross-linker, the catalyst and the cross-linker being present in the uncured blend composition in sufficient amount to cause the cross-linking reaction to occur, and (E) barium sulfate.

2. The implantable medical catheter of claim 1 wherein in the polysiloxane copolymer the —$R_1R_2SiO$— group is —$(CH_3)_2SiO$—, the —$R_3R_4SiO$— group is —$CH_3(CH_2$=$CH)SiO$—, and the $R_5R_6R_7SiO$— group is —$(CH_3)_2(CH_2$=$CH)SiO$—.

3. The implantable medical catheter of claim 2 where the —$CH_3(CH_2$=$CH)SiO$— group is present in the proportion of 0.142 mol percent in the polysiloxane copolymer.

4. The implantable medical catheter of claim 1 where the silyliated silica includes trimethylsilyl groups in such quantity that the carbon content of the silyliated silica is in the range of approximately 4 to 8 percent by weight of the silyliated silica.

5. The implantable medical catheter of claim 4 where the carbon content of the silyliated silica is approximately 7.3 percent by weight of the silyliated silica.

6. The implantable medical catheter of claim 1, wherein the barium sulfate comprises about 13% by weight of the catheter.

7. The implantable medical catheter of claim 1, further comprising an implantable fluid access port.

8. The implantable medical catheter of claim 1, wherein the catheter is in fluid communication with an implantable access port.

9. The implantable medical catheter of claim 1, wherein the catheter is in fluid communication with an implantable pump.

10. An implantable medical device comprising a catheter and an implantable access port, the catheter being in fluid communication with the implantable fluid access port, the catheter having at least one fluid passageway, the fluid passageway having an open proximal region and an open distal region and comprising a cured elastomer composition obtained by cross-linking an uncured blend composition that comprises an intimately admixed mixture that comprises the following components:

(A) silica that had been silyliated by treatment and contains trialkylsilyl groups comprising approximately 23 to 45 percent by weight of the mixture;

(B) a polysiloxane copolymer composed of divalent —$R_1R_2SiO$—, divalent —$R_3R_4SiO$— and end-blocking $R_5R_6R_7SiO$— units, comprising approximately 55 to 77 percent by weight of the mixture, where $R_1$ and $R_2$ independently are lower alkyl of 1 to 6 carbons, phenyl or trifluoropropyl, $R_3$ is vinyl, allyl, or other olefinic group having up to 4 carbons, $R_4$ is lower alkyl of 1 to 6 carbons, phenyl or trifluoropropyl, and $R_5$, $R_6$, and $R_7$ independently are lower alkyl of 1 to 6 carbons, phenyl, vinyl, allyl, or other olefinic group having up to 4 carbons and one double bond, the polysiloxane copolymer has a degree of polymerization (D.P.) approximately in the range of 3500 to 6500, and the olefin containing —$R_3R_4SiO$— groups are present randomly distributed in the polysiloxane copolymer and approximately in the 0.05 to 0.3 mol percent range, with the provisos that when $R_1$, or $R_2$, or both represent phenyl groups then proportion of the phenyl-containing divalent siloxane units does not exceed 15 mol percent and when $R_1$ or $R_2$ or both represent trifluoropropyl groups, then the proportion of the trifluoropropyl-containing divalent siloxane units does not exceed approximately 40 mol percent in the polysiloxane copolymer, (C) a catalyst; and (D) an organohydrogen polysiloxane cross-linker, the catalyst and the cross-linker being present in the uncured blend composition in sufficient amount to cause the cross-linking reaction to occur.

11. The implantable medical device of claim 10 wherein in the polysiloxane copolymer the —$R_1R_2SiO$— group is —$(CH_3)_2SiO$—, the —$R_3R_4SiO$— group is —$CH_3(CH_2=CH)SiO$—, and the $R_5R_6R_7SiO$— group is —$(CH_3)_2(CH_2=CH)SiO$—.

12. The implantable medical device of claim 11 where the —$CH_3(CH_2=CH)SiO$— group is present in the proportion of 0.142 mol percent in the polysiloxane copolymer.

13. The implantable medical device of claim 10 where the silyliated silica includes trimethylsilyl groups in such quantity that the carbon content of the silyliated silica is in the range of approximately 4 to 8 percent by weight of the silyliated silica.

14. The implantable medical device of claim 13 where the carbon content of the silyliated silica is approximately 7.3 percent by weight of the silyliated silica.

15. The implantable medical device of claim 10 further comprising at least one spinal anchor, the force at the spinal anchor due to independent motion of the implantable fluid access port being about 35% less for the catheter than a catheter made of an elastomer not having the admixture of components (A) through (D).

16. An implantable medical device comprising a catheter and an implantable pump, the catheter being in fluid communication with the implantable pump, the catheter having at least one fluid passageway, the fluid passageway having an open proximal region and an open distal region and comprising a cured elastomer composition obtained by cross-linking an uncured blend composition that comprises an intimately admixed mixture that comprises the following components:

(A) silica that had been silyliated by treatment and contains trialkylsilyl groups comprising approximately 23 to 45 percent by weight of the mixture;

(B) a polysiloxane copolymer composed of divalent —$R_1R_2SiO$—, divalent —$R_3R_4SiO$— and end-blocking $R_5R_6R_7SiO$— units, comprising approximately 55 to 77 percent by weight of the mixture, where $R_1$ and $R_2$ independently are lower alkyl of 1 to 6 carbons, phenyl or trifluoropropyl, $R_3$ is vinyl, allyl, or other olefinic group having up to 4 carbons, $R_4$ is lower alkyl of 1 to 6 carbons, phenyl or trifluoropropyl, and $R_5$, $R_6$, and $R_7$ independently are lower alkyl of 1 to 6 carbons, phenyl, vinyl, allyl, or other olefinic group having up to 4 carbons and one double bond, the polysiloxane copolymer has a degree of polymerization (D.P.) approximately in the range of 3500 to 6500, and the olefin containing —$R_3R_4SiO$— groups are present randomly distributed in the polysiloxane copolymer and approximately in the 0.05 to 0.3 mol percent range, with the provisos that when $R_1$, or $R_2$, or both represent phenyl groups then proportion of the phenyl-containing divalent siloxane units does not exceed 15 mol percent and when $R_1$ or $R_2$ or both represent trifluoropropyl groups, then the proportion of the trifluoropropyl-containing divalent siloxane units does not exceed approximately 40 mol percent in the polysiloxane copolymer;

(C) a catalyst; and (D) an organohydrogen polysiloxane cross-linker, the catalyst and the cross-linker being present in the uncured blend composition in sufficient amount to cause the cross-linking reaction to occur.

17. The implantable medical device of claim 16 wherein in the polysiloxane copolymer the —$R_1R_2SiO$— group is —$(CH_3)_2SiO$—, the —$R_3R_4SiO$— group is ——$CH_3(CH_2=CH)SiO$—, and the $R_5R_6R_7SiO$— group is —$(CH_3)_2(CH_2=CH)SiO$—.

18. The implantable medical device of claim 17 where the —$CH_3(CH_2=CH)SiO$— group is present in the proportion of 0.142 mol percent in the polysiloxane copolymer.

19. The implantable medical device of claim 16 where the silyliated silica includes trimethylsilyl groups in such quantity that the carbon content of the silyliated silica is in the range of approximately 4 to 8 percent by weight of the silyliated silica.

20. The implantable medical device of claim 19, where the carbon content of the silyliated silica is approximately 7.3 percent by weight of the silyliated silica.

21. The implantable medical device of claim 16 further comprising at least one spinal anchor, the force at the spinal anchor due to independent motion of the implantable pump being about 35% less for the catheter than a catheter made of an elastomer not having the admixture of components (A) through (D).

* * * * *